(12) United States Patent
Rodriguez-Villegas et al.

(10) Patent No.: US 10,226,225 B2
(45) Date of Patent: Mar. 12, 2019

(54) FEATURE CHARACTERIZATION FOR BREATHING MONITOR

(75) Inventors: Esther Rodriguez-Villegas, London (GB); Eduardo Aguilar Pelaez, London (GB); Guangwei Chen, Guangzhou (CN)

(73) Assignee: ACURABLE LIMITED, London (GB)

( * ) Notice: Subject to any disclaimer, the term of this patent is extended or adjusted under 35 U.S.C. 154(b) by 1546 days.

(21) Appl. No.: 13/810,075

(22) PCT Filed: Jul. 14, 2011

(86) PCT No.: PCT/GB2011/001056
§ 371 (c)(1),
(2), (4) Date: Aug. 27, 2013

(87) PCT Pub. No.: WO2012/007719
PCT Pub. Date: Jan. 19, 2012

(65) Prior Publication Data
US 2013/0331722 A1 Dec. 12, 2013

(30) Foreign Application Priority Data

Jul. 14, 2010 (GB) .................... 1011816.4

(51) Int. Cl.
| | | |
|---|---|---|
| *A61B 5/08* | (2006.01) | |
| *A61B 5/113* | (2006.01) | |
| *A61B 7/04* | (2006.01) | |
| *G06F 19/00* | (2018.01) | |
| *G16H 40/67* | (2018.01) | |

(Continued)

(52) U.S. Cl.
CPC ............ *A61B 7/003* (2013.01); *A61B 5/0022* (2013.01); *A61B 5/08* (2013.01); *A61B 5/113* (2013.01); *A61B 5/7282* (2013.01); *A61B 7/04* (2013.01); *G06F 19/00* (2013.01); *G16H 40/67* (2018.01); *A61B 5/0816* (2013.01); *A61B 5/0826* (2013.01);
(Continued)

(58) Field of Classification Search
CPC .. A61B 7/003; A61B 5/08; A61B 7/04; A61B 5/0022; A61B 5/113; A61B 5/7282; A61B 5/0816; A61B 5/0826; A61B 5/4836; A61B 2562/0219
USPC .................................................. 600/529–543
See application file for complete search history.

(56) References Cited

U.S. PATENT DOCUMENTS 5,143,078 A * 9/1992 Mather ................ A61B 5/0816
600/484
6,168,568 B1 * 1/2001 Gavriely ................ A61B 5/087
600/529

(Continued)

FOREIGN PATENT DOCUMENTS

EP 0956820 11/1999
WO WO 02/30280 4/2002

(Continued)

OTHER PUBLICATIONS

Monotonicity definition.*

(Continued)

*Primary Examiner* — Navin Natnithithadha
(74) *Attorney, Agent, or Firm* — DLA Piper LLP US

(57) ABSTRACT

A method of identifying a breath comprises sensing a signal generated by a living human or animal body and separating the signal into a plurality of frequency bands to identify a breath candidate.

23 Claims, 6 Drawing Sheets

(51) Int. Cl.
*A61B 7/00* (2006.01)
*A61B 5/00* (2006.01)
(52) U.S. Cl.
CPC ..... *A61B 5/4836* (2013.01); *A61B 2562/0219* (2013.01)

(56) References Cited

U.S. PATENT DOCUMENTS

| | | | | |
|---|---|---|---|---|
| 6,241,683 | B1* | 6/2001 | Macklem | A61B 5/091 600/529 |
| 6,443,907 | B1 | 9/2002 | Mansy et al. | |
| 7,077,810 | B2* | 7/2006 | Lange | A61B 5/0823 600/538 |
| 8,177,724 | B2* | 5/2012 | Derchak | A61B 5/1135 600/529 |
| 9,585,617 | B2* | 3/2017 | Babaeizadeh | A61B 5/0836 |
| 9,649,087 | B2* | 5/2017 | Alshaer | A61B 7/003 |
| 9,801,590 | B2* | 10/2017 | Alshaer | A61B 5/7282 |
| 2003/0018276 | A1 | 1/2003 | Mansy et al. | |
| 2004/0010202 | A1 | 1/2004 | Nakatani et al. | |
| 2005/0119586 | A1* | 6/2005 | Coyle | A61B 5/0806 600/538 |
| 2006/0198533 | A1* | 9/2006 | Wang | A61B 7/00 381/67 |
| 2007/0287896 | A1* | 12/2007 | Derchak | A61B 5/1135 600/301 |
| 2010/0152600 | A1* | 6/2010 | Droitcour | A61B 5/05 600/534 |
| 2010/0240999 | A1* | 9/2010 | Droitcour | A61B 5/05 600/453 |
| 2010/0249630 | A1* | 9/2010 | Droitcour | A61B 5/05 600/529 |
| 2010/0249633 | A1* | 9/2010 | Droitcour | A61B 5/05 600/534 |
| 2010/0292568 | A1* | 11/2010 | Droitcour | A61B 5/05 600/425 |
| 2011/0288431 | A1* | 11/2011 | Alshaer | A61B 5/0803 600/534 |
| 2013/0281874 | A1* | 10/2013 | Nishida | A61B 7/003 600/534 |
| 2013/0281883 | A1* | 10/2013 | Nishida | A61B 5/7282 600/586 |
| 2013/0324873 | A1* | 12/2013 | Babaeizadeh | A61B 5/0836 600/532 |

FOREIGN PATENT DOCUMENTS

| | | |
|---|---|---|
| WO | WO 2007/099314 | 9/2007 |
| WO | WO 2010054481 | 5/2010 |

OTHER PUBLICATIONS

International Search Report and Written Opinion of PCT/GB2011/001056 dated Dec. 9, 2011.

International Preliminary Report on Patentability of PCT/GB2011/001056 dated Jan. 13, 2013.

Phil Corbishley et al., "Breathing Detection: Towards a Miniaturized, Wearable, Battery-Operated Monitoring System", IEEE Transactions on Biomedical Engineering, IEEE Sevice Center, Piscataway, NJ, USA, vol. 55, No. 1, Jan. 1, 2008, pp. 196-204.

* cited by examiner

FEATURE CHARACTERIZATION FOR BREATHING MONITOR

CROSS REFERENCE TO RELATED APPLICATIONS

This application is a U.S. National Stage Application of International Application No. PCT/GB2011/001056 filed Jul. 14, 2011. PCT/GB2011/001056 claims priority from Great Britain Patent Application No. 1011816.4 filed Jul. 14, 2010.

The invention relates to a system, method and apparatus for monitoring respiratory activity.

Monitoring respiratory activity is of importance, for example, in detecting and measuring: central apneas, that is, cessation of breathing which can occur during and after an epileptic seizure, in sudden infant death syndrome and in other instances; obstructive apneas, mixed apneas or hypopneas, which can occur for example when someone suffers sleep apnea; Cheyne-Stoke respirations which can be associated with brain tumors or critical medical scenarios; paradoxical breathing which may be seen in children with respiratory distress and patients with chronic airways obstruction; reduced respiratory drive for example in recovery rooms after anesthesia; abnormal breathing rates which can be used in early warning score systems; and many other medical and non-medical scenarios.

WO2007/099314 proposes a method and apparatus for detecting respiration. The apparatus obtains a respiration sound signal. The respiration sound signal is then processed to identify a frequency and amplitude component. An intermediate region between normal breath sounds and no detected breath sounds is identified by identifying start and end points of a breath signal and processing the signal accordingly. However, in some instances the start or end point may be incorrectly identified, and/or respiratory pauses incorrectly detected and classified as breathing events, and/or respiratory events incorrectly detected and classified as respiratory pauses, and/or noise/interference may be incorrectly detected and classified as breathing or respiratory pauses.

The invention is set out in the claims.

Embodiments of the invention will now be described, by way of example, with reference to the drawings of which:

Figure 1:
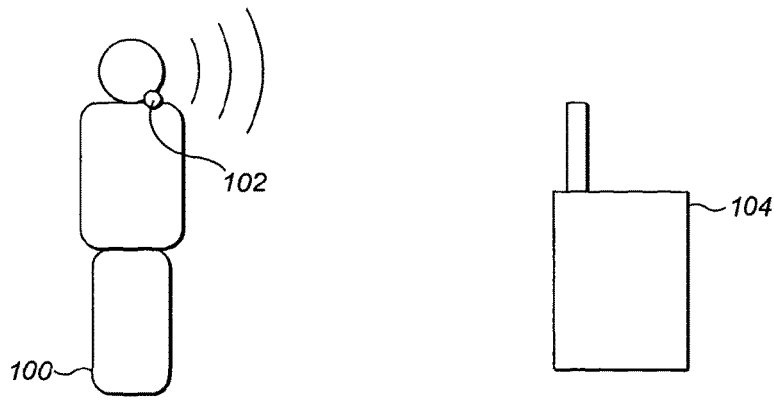
FIG. 1 shows a system overview.
Figure 11:
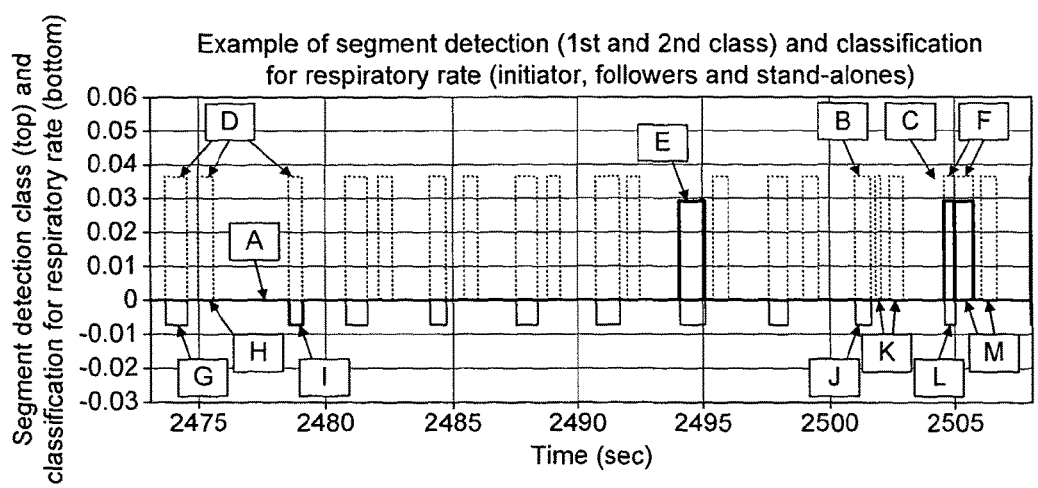

FIG. 11 shows a sequence of breath segments detections along with their classification by the respiratory rate routine An overview of the system is shown in FIG. 1. An individual 100 whose respiratory activity is monitored carries a respiration detector 102 to detect respiratory activity. The detector 102 sends a signal, by any appropriate means for example telemetry networks such as a mobile phone network, to a base station 104 which then takes the appropriate action as required and can display instantaneous acquired data or stored data as well as results of analysis thereof and other related information. For example where the monitor detects cessation of breathing an alarm signal can be raised; or the breathing signal can be stored over a period of time for long term analysis; or the sound of breathing could be played back. In the case of the alarm this may be accompanied by patient treatment such as administration of a mild electric shock or generation of an acoustic alarm to wake the patient up.

Additionally the signal (or fractions of it) in processed or unprocessed form, or parameters related to it could be locally stored in the sensor's end. For example, the signal could be directly processed in the sensor end and the numbers of expirations meeting predetermined criteria, for example with tidal volume below a certain value, such as 0.2 liters, during a certain interval of monitoring could be locally stored, either on its own, or together with fractions of the raw signal corresponding to intervals of time during which the tidal volume is lower. Alternatively this information could be transmitted to a base station carried by the patient, or directly to a doctor or a carer, either in real time or on request.

The necessary processing apparatus may be included in either the detector 102 or the base station 104 or in any suitable part of the system. In embodiments the detector 102 will at least include one or more microphones or any sensor or equivalent means such as an accelerometer that can measure relevant parameters such as sound or vibration for detecting breath and attachment means to both position the sensor in a suitable location to detect breath sounds or other signals and optimize long time body attachment and comfortability, as well as ensure or enhance signal transmission (for example providing an optimum acoustic seal). Any appropriate location and design of detector can be adopted.

In overview the method described herein for breathing detection and analysis of breathing characteristics is based on a multi characteristic analysis of signals generated by the human or animal body.

Firstly, the signal is split into several, for example four, frequency bands and then the different bands are separately subjected to initial processing. The bands are not necessarily independent, i.e. there can be some degree of overlapping between them. For example, one band could go from 100 Hz to 200 Hz and another band could go from 150 Hz to 250 Hz. Part of the initial processing can include subtracting interference that can be initially modelled with an analytical function. An example could be known electromagnetic environmental interference. It can also include eliminating residual offset created by for example hardware elements in the processing chain. The absolute value of the signals referred to their DC point within the bands can be taken or alternatively they can be subjected to rectification. After any of these steps, all the signals above a certain frequency can be eliminated or smoothed out. Finally if the original signal was sampled, at this stage, the signal can be downsampled. It will be appreciated that each of these steps can be adopted or omitted as appropriate. For example downsampling is not always required. The signal may not have been sampled at all from the start, in which case this wouldn't apply.

Secondly, the processed signal within the different bands is analysed by an algorithm such as a segmentation algorithm (all or parts of which could be realized either in software or directly in hardware). The results of this analysis are used to define segments of the original sensed signal as candidate breaths (i.e. parts of the signal that could correspond to breath) or respiratory pauses (i.e. parts of the signal that could correspond to periods between inspiration and expiration or between two different breaths) or just noise or interference (i.e. part of the signal that is corrupted by other events so it is not possible to fully decide whether it correspond to respiratory events, respiratory pause, or other artifacts, such as for example by signals generated by other organs). The segmentation algorithm thus defines the start and end points more accurately than in known approaches.

Following the segmentation algorithm candidate segments are evaluated further within a certain time interval in order to define whether they should be considered as a certain breath event or not. For example, a candidate event may correspond to an inspiration or an expiration. Also, a certain sequence of candidate events with some characteristics, like reduced power, for an extended period of time may correspond to a hypopnoea event. Absence of candidate breaths events for an extended period of time with all characteristics within certain ranges may correspond to an apnea and hence require triggering of an alarm. Each of these gives a useful result and information for monitoring respiratory activity which can be accepted or disregarded as appropriate in evaluating breathing. As multiple channels are obtained, relationships between signal characteristics for different channels can be analyzed. (The terms "band" and "channel" are used interchangeably herein and will generally refer to all frequency components between a start and stop frequency of a signal which has been further subjected to the initial processing described above).

The system allows transmission or storage of raw or processed data and in one or multiple channels. As discussed in more detail below, the channels are analyzed to find several parameters which are then compared between each other, or to certain threshold or boundary conditions. Examples could be: ratios of certain functions of energy/power between different channel signals, which for example need to fit a certain function; envelope shape comparison (the shape between the envelopes of the processed signals within the different channels should follow a certain trend for the segment to be considered as breath); comparison of minimum or maximum related parameters with dynamic thresholds (the dynamic thresholds are defined based on the previous breath segments that were considered as candidate events with a certain degree of probability, except at the beginning of the process, i.e. when no breath segment has been detected yet, when either fixed values can be considered or alternatively they can be calculated as a function of a set of parameters extracted from the acquired signals following the start of operation); comparison with different dynamically updated noise floors for each of the channels; patterns followed by the signals in different channels.

Overall, these features combined result in a versatile algorithm which is robust and independent of subject specific signal characteristic; or circumstance changes; as well as external and internal artifacts such as music, rubbing or movement and speech so that there is no need to calibrate between person to person.

Turning to the approach in more detail, the continuously detected signal is processed to segment an individual occurrence of a possible breath, inspiration or expiration. These are then assessed to determine whether they are actual breath signals, or "candidate breaths" (i.e. they are likely to be breath events with a variable degree of probability). Candidate breaths can then be further analyzed for respiratory monitoring. It is not necessary that breath sound segments are processed by all of the stages of the system. However, each stage will provide more information and allow the system to have increased sensitivity and/or specificity in determining respiration and/or identifying a particular respiratory event, such as inspiration, expiration or other (i.e. each stage will increase the probability of a certain "candidate event" being a true event).

Figure 2:
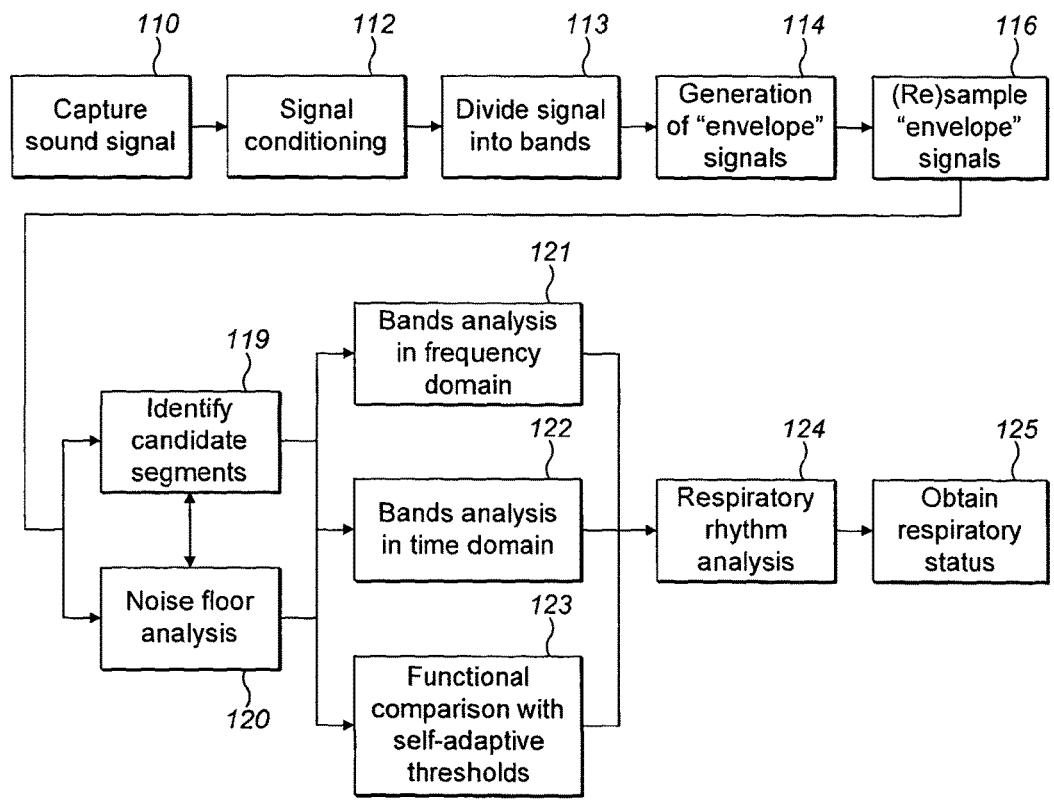
FIG. 2 shows a simplified flow diagram of the breath related signal processing steps.

The main steps are shown at FIG. 2 as comprising capturing body generated signals (step 110) using the detector 102 (FIG. 1), initial splitting the signal into frequency bands (which can have overlapping between them) (step 113), with some previous pre-processing that may include removing any interference that can be analytically modeled (step 112), some further pre-processing of the bands, which can include further elimination of residual DC offset, taking the absolute value or rectifying the signal or equivalent, within the bands and smoothing the signals which can be done by removing frequencies above a certain one (step 114), down sampling (step 116) of the shaped signal (this is only necessary of course if the signal was originally sampled), parallel segmentation of the signal and noise floor analysis (steps 119 and 120) and then analyzing the signals according to one or more relationships between parameters in the different channels and how some of them relate to dynamically updated thresholds. The analysis steps can include frequency (step 121) and time domain (step 122) analysis, and comparison with self-adaptive thresholds (step 123) which can be performed parallel to respiratory rhythm analysis (step 124) to obtain respiratory status/information (step 125). Each of these steps is described in more detail below with reference to the remaining figures. It will be clear from FIG. 2 however that steps 110 to 116 are preferably performed sequentially while others can be performed in parallel.

The body generated breath related signal, for example sound, is captured at step 110—this is typically performed continuously. Afterwards, the first goal of the process is to attenuate as much as possible the non-breathing signal which may be also captured by the sensor system without compromising the breathing signal. This can be done in many different and complementary ways. For example, a high pass filter could be used to eliminate low frequency interference components such as mains electromagnetic interference. Also any other electromagnetic interference that could be modeled but not filtered because it falls within the signal's frequency bands, could be directly subtracted from it. An example could be electrical interference resulting from digital circuitry built into the sensor. If this falls within the signal's band it could be either eliminated with a high order notch filter, or alternatively, since it can be predicted, subtracted from the signal.

At step 113, the signal is further divided into more than one, for example three or four or more frequency band channels. Suitable band channels could be 200 Hz to 350 Hz, 300 to 500 Hz, 550 Hz to 700 Hz and 750 to 2 kHz. Note that neither the passband within a channel has to be flat, i.e. different harmonics can be scaled in a particular way, nor do different bands within different channels have to have the same shape. An example could be that in the lower frequency channel the passband is attenuated by 50% with respect to the gain of the third band. In the same way it is found that introducing a constant delay to the harmonics within the limits of the bands can help to more accurately compute differences between certain parameters (such as those related to power ratio).

After the splitting of each signal into frequency bands a certain residual offset may appear in different components, which can be eliminated for example using another high pass filter with less than 200 Hz cut-off frequency. The order of this filter can be as low as 1 (not shown). Subsequently, a power related parameter has to be extracted for each one of the bands. This can be done in different ways, involving for example obtaining the absolute value of the signal once the DC component has been eliminated, or via any method of signal rectification either in hardware or software. The next step is for each channel to smooth the signals in order to reduce fluctuation in the individual signals and capture the envelopes (step 114). Therefore, for example, a lowpass filter can be used to remove the high frequency contents of the signal (which caused the fluctuation). A possible cut-off frequency for this filter could be 5 Hz. There is no restriction on the minimum or maximum order of the filter. It should be noted that the cut-off frequency of the filter is related to the maximum and minimum breathing rate which it is necessary to accurately capture for the application, and the order will determine how much of the out-of-the band interference, such as heart signal, is removed.

Figure 3:
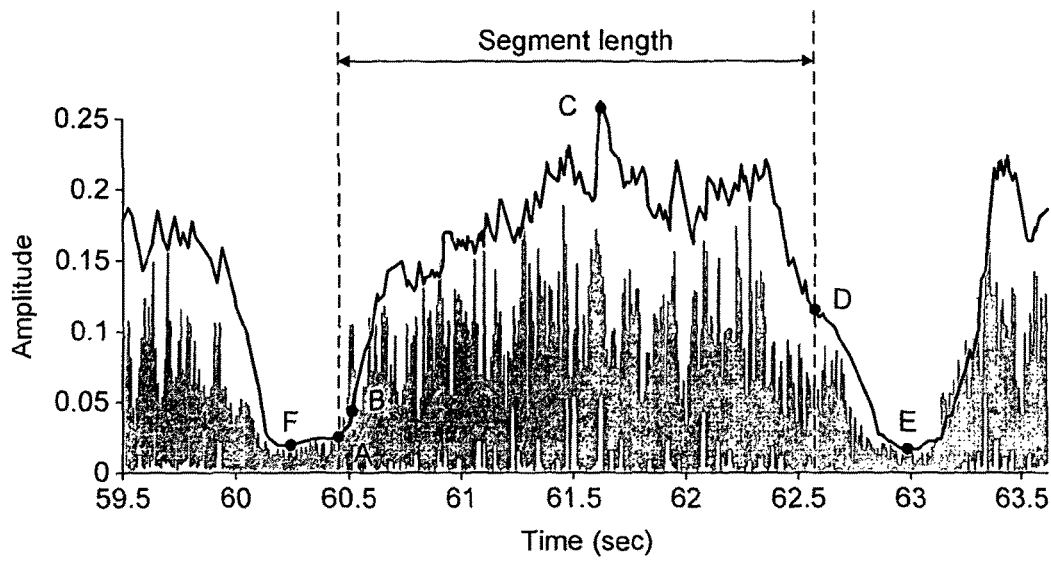
FIG. 3 shows an example of a new segment definition (original signal; envelope in one channel)

At step 116 after removing high frequency contents for each band the envelope signal can be downsampled with a lower sampling frequency to that of the first bandpass filter. In the already rectified and smoothed bands the required sampling frequency can be significantly lower than in the original signal. The final number is related to the order of the smoothing filters and the specific interference which will depend on many factors, including sensor system construction. Downsampling will have the advantage of reducing the power consumption, although it is not necessary if the original signal was not sampled. The envelope signal for a channel is shown in FIG. 3 together with the original signal. At step 119 the envelope of the signal in either one or several channels is analyzed to find the precise start and end point of candidate breath segments. In parallel, noise floor analysis 120 is performed throughout the segmentation process 119.

For the sake of clarity or simplicity, let us refer to one channel. FIG. 3 shows a single breath event (inspiration or expiration) lasting approximately from 60.4 to 62.7 seconds roughly, together with the envelope in one channel. The effective length of time for a single inspiratory or expiratory event is related to what is referred to as the segment length and the start and end points 'A' and 'D'. These are determined from the envelope signal as described below.

According to the approach described in WO2007/099314, an algorithm searches the minimum or valley-bottom position (point 'F') of the input since the end of last iteration. Next, once the input signal rises over the twice value of the minimum point, (point 'B'), the process changes to peak-seeking-finding the apex of the input signal denoted as 'C'. When the signal falls below point 'D', half of 'C', it turns back to search for the valley point 'E' again. Finally, it works out the segment length from the time difference between the two minimum points 'E' and 'F'.

However, the period might not be calculated appropriately since this method can mistakenly determine minima as the beginning and ending points of the candidate segment by assuming the breath segments appear continuously and closely. The error caused by this may exceed 50% of the actual value due to the flat input signal during a breath pause period, which can lead to failure of temporal domain recognition as well as integral related conditions.

Referring to the approach described herein and with reference to the example depicted in FIG. 3, which shows the outline of the signal in one channel, the beginning point of the segment in this particular example is located at what we refer to as "segment start point 'A', which occurs before 'B' (although if accuracy is not a problem 'A' can also be approximated by 'B'). 'B' is the point at which the signal is ready for apex seeking (FIG. 6, after 'yes' of block 810) and represents also the point at which the envelope signal has risen a certain proportion from a certain value which is related to a combination of certain identified minima in a plurality of bands. These minima do not necessarily have to be the latest ones to have been identified within a channel, since these ones may be corrupted by noise. Points such as 'B' will be referred to a "peak seeking entry point" in the following. Unlike in WO2007/099314 'B' does not necessarily have to be limited to twice the value of 'F'. The fraction of the signal just before 'B' is also characterized by a significant slope change. The ending point of the segment should be approximated by point 'D' instead of 'E', the significance of which is explained below. Unlike in WO2007/099314, 'D' is not limited to half the value of 'C'. Note also, that the ending point/time of the segment is not necessarily the ending point of the candidate event. The latter can be a scaled version of it, or it could also be approached by it plus a certain time.

Both the determination of the significant minima and the minimum slope as well as the restrictions upon them can take into account either all the channels or a subset of them. This subset can be chosen as a function of their signal to noise characteristics. Note that any significant time or signal values, such as time of occurrence of a minimum and its absolute value for one or a plurality of bands can be temporarily stored for example in a local memory or transmitted and these values can be dynamically updated as necessary.

After point 'D' has been identified the method starts again looking for "valleys" within the different bands. A valley represent an absolute minimum happening after the end of one segment and before the peak seeking entry point" of the segment under evaluation (Represented as points 'E' and 'F' in the example in FIG. 3). Once these have been found they are evaluated to see whether they correspond to valid positive turning points, i.e. turning point which can be used to determine the start point of a candidate breath segment, or not, following a method which is further discussed later on.

According to the approach described herein, a certain minimum time threshold is established, which can be the same or different between for one or several bands, as the maximum time taken by the envelope signals to rise at the beginning of an inspiration or expiration event, for example 0.2 s for bands 1 and 0.15 s for band 2. Within this time period, the envelope signals have to rise to a considerable level compared to a certain pre-established value, which is normally a function of previously found "turning points" in a plurality of bands. For example, referring to FIG. 3, which represents one of the channels, assuming the hypothetical scenario as shown in FIG. 3 in which the turning point 'A' (where the signal starts to rise) is to be evaluated as the possible start point of the candidate segment, the time from point 'A' to point 'B' where point B has a fraction, for example twice, of previously determined minimum value 'F' should be less than 0.2 s. Otherwise, any point within 0.2 s prior to point 'B' can be taken as segment start point. Note that this point 'F' is not necessarily equal to 'A' and it can correspond to a previously determined minimum or a functional combination of minimum values as it will be seen later on. In other words, in order to limit the start point locating error within a certain percentage from the shortest breath the time elapsed between the segment starting point and the point where the system find the significant rise point (such as point B), could be as low as 0.2 seconds. Additionally if there were more than one positive turning point within a certain time distance before the entry point of the peak seeking routine then the closest one is taken as the segment temporary start point (in order to further asses the validity of this point as the start point it can additionally be verified as explained later).

Figure 4:
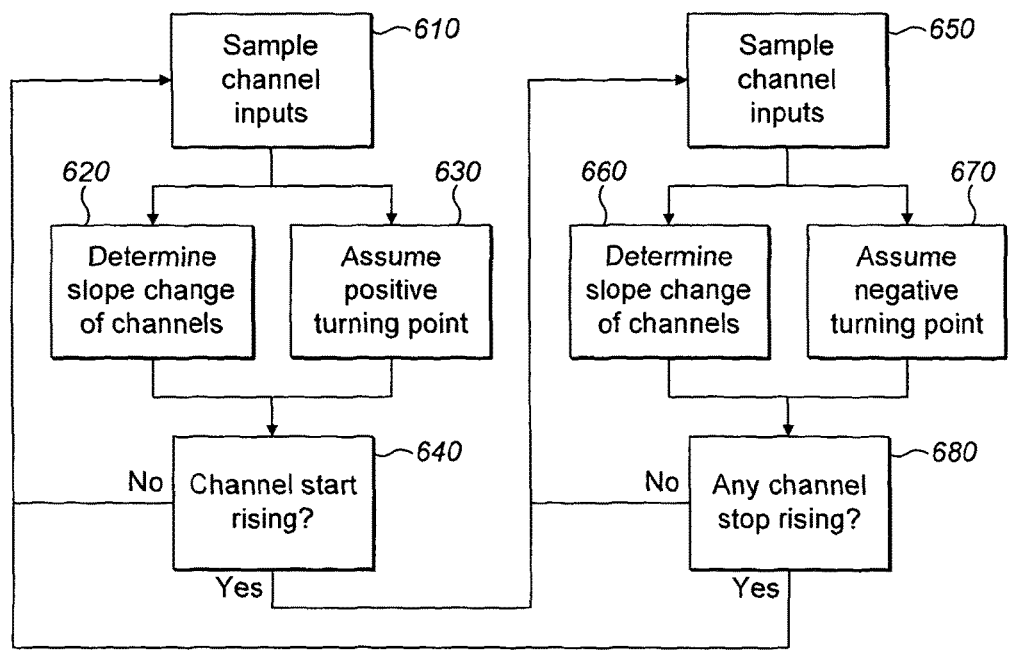
FIG. 4 shows a flowchart of turning points detection.

Positive or rising "turning" points (effectively relative minima) can be found following a method such as the one as shown in FIG. 4. Changes in slope of the envelope signals from at least two channels are evaluated at regular intervals. Measuring the slope can be done for example taking samples from at least two of the channels 610 at regular intervals and evaluating the difference at step 620, for example with a time distance of 20 samples. This is used to determine the degree of monotonicity of the signals, i.e. whether the signal is mostly increasing or decreasing. Of course, evaluation could also be done in the continuous time domain, i.e., sampling would not be needed. Before step 640 is evaluated, any point inside the 20 samples window could be the positive turning point. For example, the minimum point in the window can be assumed as the positive turning point at step 630. Once at step 640 if the change is positive, the result of positive turning point is latched.

Negative turning points (effectively relative maxima) can be found following an equivalent procedure as depicted in steps 650, 660, 670 and 680. In this case, the slopes of the channels are continuously being monitored until a negative trend with the same time window is found. Generally, once a negative turning point is found the search for a negative turning point will start and vice versa reinitializing the whole process from steps 610 or 650 respectively.

Figure 5:
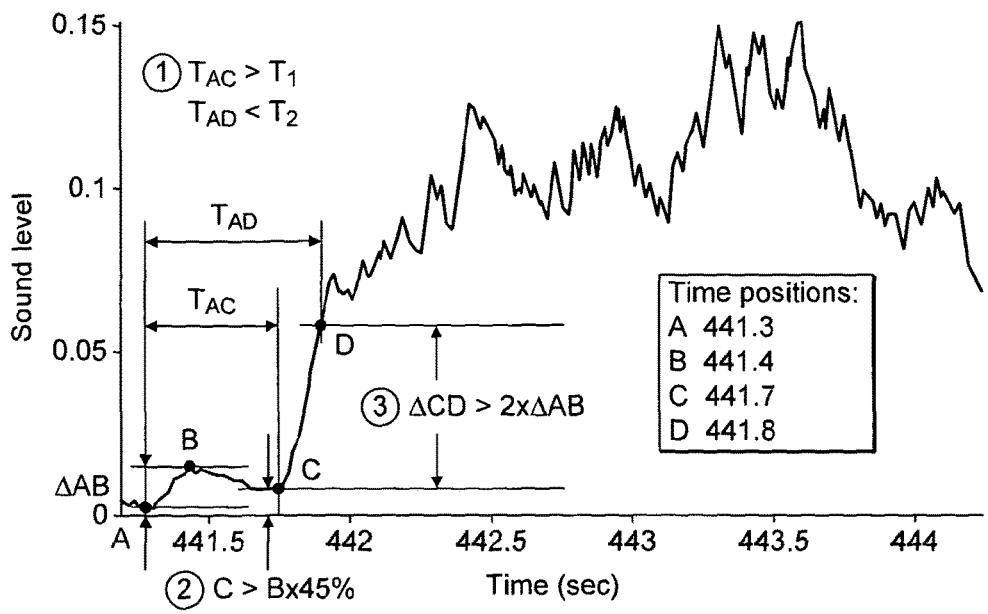
FIG. 5 shows a processed (envelope) one channel signal with an ambiguous starting point.

However, it cannot always be guaranteed that the right segment starting position (determined either from one, or from a combination of channels) can be found just by satisfying the assumptions discussed above. An exception is shown in FIG. 5 where noise corrupts the beginning of the segment. The method could find a wrong starting point 'A' for the segment accidentally, for example, if the noise floor had increased. Usually, the exception will happen when the noise floor is low. Because of this, verification of the temporary start point found before the peak seeking entry point is beneficial for high sensitivity applications to overcome the problem. Firstly, the maximum change ($\Delta_{AB}$ in FIG. 5) of a signal related to a possible starting point 'A' is recorded for a certain time threshold, as an example 0.1 second, or $T_1$ in FIG. 5. After that, the method tries to find another positive turning point 'C' whilst at the same time searching for an apex. Once a new turning point is found the differences between the instantaneous value of the envelope signal and the value of the new turning point 'C' are evaluated for the shortest of the following time periods:

1—Until a point 'D' is detected for which the difference $\Delta_{CD}$ exceeds the previous change $\Delta_{AB}$; within a certain percentage (for example, as shown in the FIG. 5 double)
2—Until a certain time threshold ($T_2$ in FIG. 5) is reached.
3—Until the signal has fallen below the threshold for the segment end point (explained in subsequent paragraphs)
If 1— is shorter or equal to 2 and shorter than —3—, then 'C' will replace the old starting point 'A', hence becoming the new valid turning point and the whole verification process will restart from it. If either 2— or 3— are shorter than 1— then 'A' has been verified as the valid turning point.

The apex can be found by finding maximums in the envelopes, in such a way that if a new maximum is found this one may replace the previous one as a candidate apex if the signal in-between in one of several bands has not fallen to more than a certain percentage of their respective candidate apex in one or several bands or a combination of the apex in more than one band. However, if before a new maximum is found the signal has fallen to more than a certain percentage of their respective apex in one or several bands or a combination of the apex in more than one band, then the search for the apex may end, with the candidate apex becoming the identified one. This is further explained later in the text.

The seeking of the end point of a segmented breath signal is as complex as seeking for the segment starting point because the signal to noise ratio SNR tends to be low, i.e. it is difficult to differentiate the signal from the noise. Hence, it is very difficult to terminate the segment exactly. Rather than determining the end precisely, it is much easier to close the segment at the time that the SNR is below a certain threshold. This decision can be based on one or several bands, and the threshold may be equal, or different depending on the bands.

Therefore, the end point may be set at the point where the signal drops to less than a certain percentage of the apex value ('C' in FIG. 3), for example 30%. But, if the 30% of the apex value is not higher than the value recorded at the segment starting point, this threshold can be replaced by the initial value in the segment.

Additionally, from time to time the noise floors of the channels may vary making it difficult to find the positions for the points based on just its most adjacent maxima and minima. A critical situation could happen when the SNR of the channels drops below a certain value. In this situation the threshold for seeking point 'B' (as in FIG. 3) which helps to define the segment start may be too high whereas the threshold for finding the segment end point 'D' may be too low. Such points 'B' and 'D' would then not visible from the envelope signal, because of the high noise floor. To overcome this weakness, the threshold of the peak seeking entry point (i.e. point 'B') can be determined by the end point of the previous segment. Similarly, the threshold for a segment end (i.e. point 'D') can not be smaller than the point 'B' of the same segment. These two together make the segmentation method more robust to variations of noise floor.

An alternative way of finding the end point, which may be useful for certain applications can be based on monitoring the slope of the signal at the point at which it has fallen to any of the values described in the previous paragraph and subsequent points after that. The end point can be determined as the point at which the absolute value of the slope decreases to a certain percentage of the slope monitored in the first point.

Figure 6:
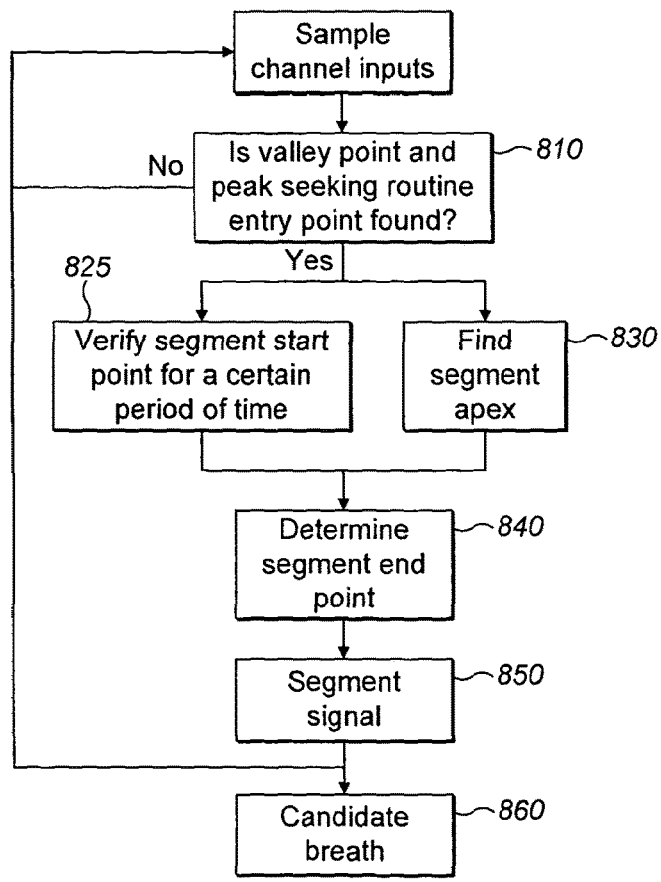
FIG. 6 shows a basic routine for a segmentation algorithm.

FIG. 6 shows a simplified block diagram of the full routine for obtaining start and end points of candidate breath segments (without including noise related techniques). These can then be further analyzed by the routines described with reference to FIG. 2.

The signal is taken and a valley in the signal together with the position of the peak entry point are being found at step 810. A temporary start point will be chosen based on this which will have to be further verified and updated if necessary at step 825, while simultaneously looking for the apex at step 830. Once the apex is determined, the segment end point can also be found (step 840) as the point at which the signal falls below a certain value which can either be a percentage of the apex point, or a percentage of the previously found peak seeking entry point, or a percentage of a combination of previous valley points found within the bands, or a point at which there has been a significant slope change.

The signal is segmented at step 850 from the start point to the end point. The information in each of the channels can now be used to assess a 'candidate breath event' as a fraction of the original sensed signal which contains an identified segment or a fraction of it and has a duration which is within certain pre-established limits. This returns a 'candidate breath' event 860. For example, a "candidate breath event" may be identified as the portion of the original signal between the start and the end point of the segment if the duration of the segment is between 0.3 s and 10 s. The routine then returns to finding a valley 810 to begin identifying more 'candidate breaths'.

We now have a signal that is representative of single breaths. However, even though the signal has already been filtered there will still be a certain level of noise within the signal. The noise will not be constant over time and will be made of both background interference and noise introduced by the system itself, which is termed collectively the "noise floor". The noise floor will also vary between the different channels and so is determined independently for each one of them. According to FIG. 2 this is done at step 120 as described in more detail below.

Empirically the noise floor can be observed as the minimum of the envelope signal within respiratory pause sections between breath candidate segments. Under normal circumstances there is a time gap between each segment, as discussed above, that contains the lowest point of the signal. In one embodiment the RMS power, or a function of it during these time gaps could for example be used estimate of the noise floor.

Figure 8:
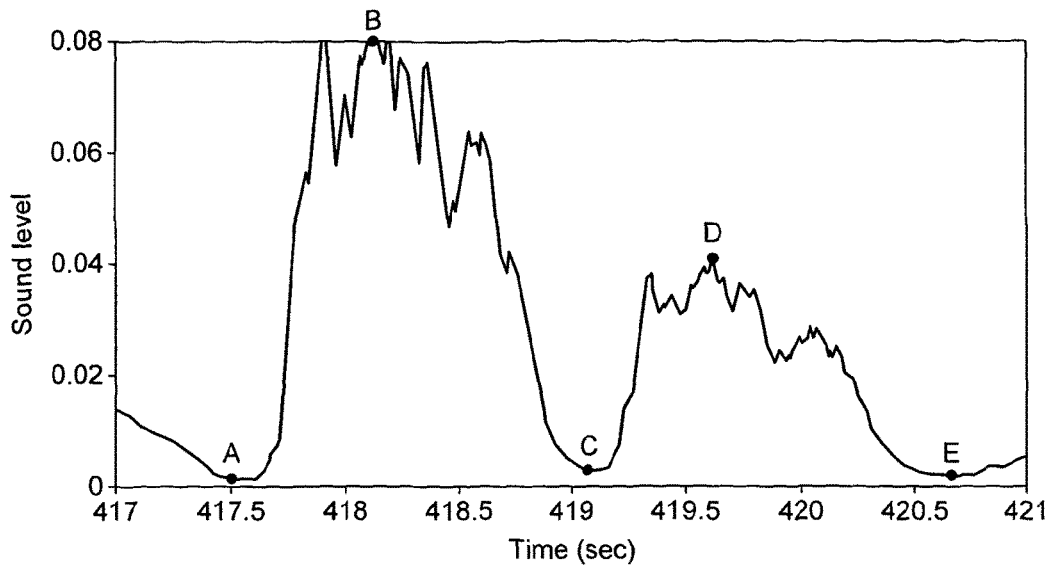
FIG. 8 shows the envelope from one of the channels for a respiratory cycle.

When identifying a pause section, it is noted that, generally, the respiratory pauses between the inspired and expired breath are shorter than the pause between each full respiratory cycle. Also, the breathing pause within a respiratory cycle may be too short for the envelope signal to reach a true minimum due to hardware delay. This can lead to a wrong noise estimation if short time frames for noise evaluation are considered. This is illustrated in FIG. 8 which shows an envelope signal of a complete single breath including inspiration and expiration. The figure starts with a respiratory pause, then the level rises sharply from A to B due to inspiration. Before expiring a person normally pauses and the signal will fall causing a local minimum C before another maximum D during expiration, and another minimum E when the whole respiratory phase finishes. The time frame for noise floor estimation and values updating should be long enough to cover at least one respiratory cycle composed of two peak segments and three breathing pauses and hence all the relevant minima should be stored. The value of the noise floor estimates is calculated from the minimum of these buffer values and used for the entire breath cycle. The estimated noise floor can optionally be removed from the signal for each of the channels.

Further steps can be added to the method in order to increase the probability of assessing correctly whether a candidate event is a true event.

Referring to step 121 of FIG. 2 we can compare the relationship between functions of power of the envelope signals for identified segments within different channels which are defined by frequency bands with predetermined boundaries. Hence if the ratios are within the boundaries the event is more likely to be an inspiratory or expiratory event than if it is outside the boundaries. These boundaries can also be different for inspiration and expiration. An example of a possible method to do this is described in the following equation. If the signal is sampled, within a segment the power for one band after removing noise is related to:

$$P(CHi)_{RMS} \text{ of} \tag{1}$$

$$\text{channel } i \propto \sum_{n=\text{Segment Start}}^{\text{Segment End}} (CH_i(n) - CH_i \text{ Noise Floor})$$

where $$CH_i(n) = \sqrt{\text{Power of channel}_i(n)} = \text{Envelope Signal}_i(n)$$

and n is the sample number.

Figure 9:
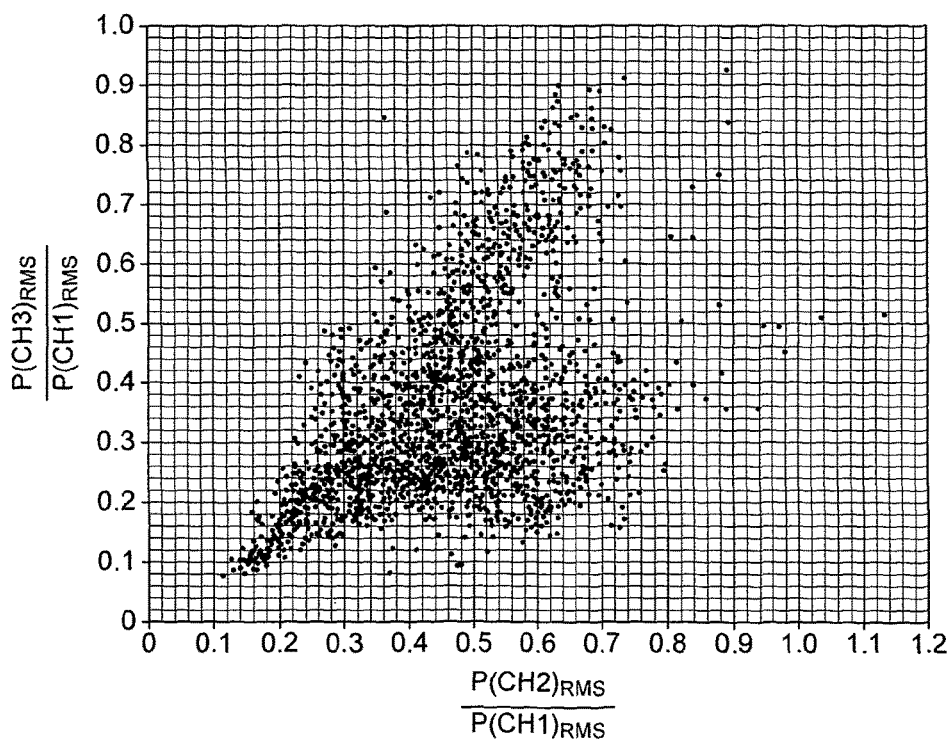
FIG. 9 shows a distribution of breath overtones (with noise floor reduction)

FIG. 9 shows an example of the relationship between two possible sections of respiratory overtones, 300 Hz to 500 Hz (Channel 2) and 550 Hz to 700 Hz (Channel 3) (both normalized against the 200 Hz to 350 Hz band (Channel 1 in this example, although it could be another channel)), where the X and Y values are given by:

$$X = \frac{P(CH2)_{RMS}}{P(CH1)_{RMS}} \tag{2}$$

$$\approx \frac{\sum_{\text{Segment Start}}^{\text{Segment End}} (CH2 - CH2 \text{ Noise Floor})}{\sum_{\text{Segment Start}}^{\text{Segment End}} (CH1 - CH1 \text{ Noise Floor})}$$

$$Y = \frac{P(CH3)_{RMS}}{P(CH1)_{RMS}} \tag{3}$$

$$\approx \frac{\sum_{\text{Segment Start}}^{\text{Segment End}} (CH3 - CH3 \text{ Noise Floor})}{\sum_{\text{Segment Start}}^{\text{Segment End}} (CH1 - CH1 \text{ Noise Floor})}$$

The channels are compared using the ratios given in equations 2 and 3 above and plotted on the graph. FIG. 9 shows an example of possible instances of power distribution for candidate segments over two of a plurality of bands: channel 2 (x) and channel 3 (y) each compared with channel 1.

It can be seen that the breaths are concentrated in the region between 0.06>Y>1 and 0.1>X>1.2

Figure 10:
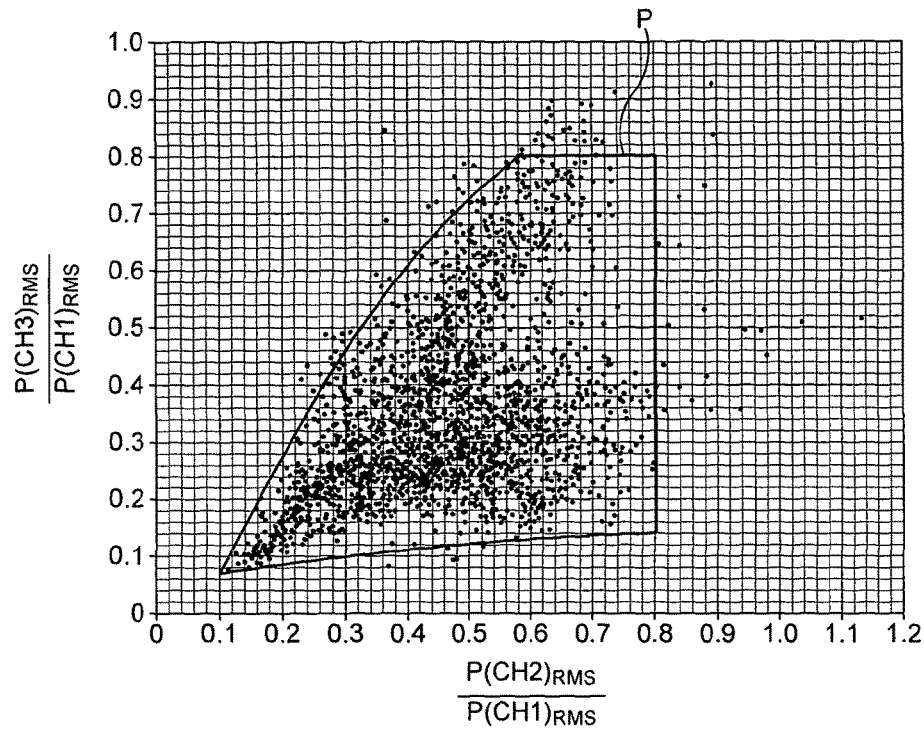
FIG. 10 shows an example of limiting area of spectral power distribution for three channels.

The density of dots in FIG. 9 is related to the probability for that signal with the particular power distribution is caused by breathing. The figure shows that most breath signals have a pattern of power distribution concentrated in a limited area. A boundary line 'P' can be developed as shown in FIG. 10 surrounding the concentration of dots that defines the version of most likely "power related" distribution. The boundary region can be approximated by at least two polynomial equations which describe upper and lower boundaries. For an increased sensitivity on breathing detection the system may be designed to only accept as valid a breath signal with characteristics contain in the area within the boundary line 'P'. Hence, in the example the dots within the boundary line can be considered to be breath signals whereas outside the boundary line the candidate breath segments are not considered to be true breath events.

This condition increases the sensitivity to detect apnea and avoid the situation in which someone may not be breathing even though the algorithm might otherwise detect it as breathing. This boundary line can also dynamically change depending on other time related conditions. For example, if a segment has a time duration smaller than a certain value, such as 0.15 s, and at the beginning of the segment a certain channel is the highest (for example channel three) then the boundary line to be considered for the relationship between the powers of that channel and another one (for example channel one) is 'P1', whereas if the duration is longer than 0.15 s, the boundary line could be 'P2'. In the same way, not all the boundary conditions have to change if one of them changes, and extra ones could be added depending on the instantaneous characteristics of the signal. Also, the boundaries can change depending on whether a specific channel within the segment under evaluation is the channel with the highest signal to noise ratio, or it is not, and if it is the latter on whether that channel has the highest value at the segment start point or not. An example of this that is found to work for certain applications could be that all the channels have to meet the following conditions to be considered as breathing segments:

1—If a channel is the one with the highest signal to noise ratio in a candidate breath segment, then this channel does not have to meet any condition.

2—If the channel is not the one with the highest signal to noise ratio and the signal in that channel has the highest value at the beginning of the segment, the ratio of its power spectral density and the power spectral density of the channel that has the highest signal to noise ratio has to be larger than 50%. Alternatively, if the signal in that channel does not have the highest value at the beginning of the segment, the ratio of its power spectral density and the power spectral density of the channel that has the highest signal to noise ratio has to be lower than 70%.

Finally, the definition of the limiting boundaries can be finely adjusted or calibrated according to the characteristic of breath signals from different people, although this is generally not necessary.

So far we have taken a captured breathing signal, pre-processed it, split it into channels, found the envelopes, segmented it into 'candidate breaths', removed background 'noise floor' from the 'candidate breaths' and then by comparing frequency related parameters for the different channels identified which of the 'candidate breaths' are more likely to be breath events.

To further confirm if the segment is a true breath sound the shape of the breath sound envelope is assessed, according to step 122 of FIG. 2 In particular the system can check that some of the bands have particular and synchronous characteristics in the time domain, for example check that the channels follow the same monotonicity trend between the beginning of a segment and a certain time determined by a different channel, as it is illustrated in the following expression for two of the channels (3 and 4), referred to the apex position of another:

$$\text{condition\_trend} = \begin{cases} (CH_4[\text{At the Apex Position of } CH_1] - CH_4[\text{Segment Start}]) > 0 \\ \text{AND} \\ (CH_3[\text{At the Apex Position of } CH_1] - CH_3[\text{Segment Start}]) > 0 \end{cases} \quad (4)$$

Hence, in this example, the signal is more likely to be a candidate breath if the channel 3 and 4 values have increased when channel 1 reaches its apex. Of course this could be extended to any number of channels, although not all of them need to be included in the AND condition.

Another condition that can be evaluated to further ascertain whether an event is likely to be a respiratory event in two or more channels that are close to each other in frequency, is the relationship between the envelope value of one of them at a time equal to the apex of another with respect to the maximum value within the segment of the other channel in close proximity. This should exceed a certain percentage, as for example shown in eq. (5).

$$\text{condition\_transient} = \left( \frac{CH4[\text{At the Apex Position of } CH_1]}{\max(CH3[\text{Seg Start}:\text{Seg End}])} \right) > 30\% \quad (5)$$

A further condition could be the relationship between the times at which the different channels reach their apex with respect to the segment. For example, the maximum time difference between different channels reaching their apex could be set to a percentage of the segments' duration, such as 5%.

The relationship between the negative slopes during the section of the signal corresponding to it fading out for different channels can also be used. This can for example be approximated by measuring the time distance between each channel's apex and the end of the segment.

Another condition that can be considered is that changes of different channels' power for example between start and apex should correlate to the spectral energy distribution. For example the change of channel 2 could be limited to the range of 20% to 200% of $$\frac{P(CH2)_{RMS}}{P(CH1)_{RMS}}$$

(with noise floor compensated); and the change of channel 3 could be limited to the range of 0% to 250%

$$\frac{P(CH3)_{RMS}}{P(CH1)_{RMS}}$$

(with noise floor compensated), this is:

$$\text{condition\_ch2\_rise} = \begin{cases} \frac{\max(CH_2[\text{Seg Start}:\text{Seg End}]) - CH_2[\text{Seg Start}]}{\max(CH_1[\text{Seg Start}:\text{Seg End}]) - CH_1[\text{Seg Start}]} > \left(20\% \times \frac{P(CH2)_{RMS}}{P(CH1)_{RMS}}\right) \\ \text{AND} \\ \frac{\max(CH_2[\text{Seg Start}:\text{Seg End}]) - CH_2[\text{Seg Start}]}{\max(CH_1[\text{Seg Start}:\text{Seg End}]) - CH_1[\text{Seg Start}]} < \left(200\% \times \frac{P(CH2)_{RMS}}{P(CH1)_{RMS}}\right) \end{cases}$$

-continued $$\text{condition\_ch3\_rise} = \begin{cases} \dfrac{\max(CH_3[\text{Seg Start}:\text{Seg End}]) - CH_3[\text{Seg Start}]}{\max(CH_1[\text{Seg Start}:\text{Seg End}]) - CH_1[\text{Seg Start}]} > \left(0\% \times \dfrac{P(CH3)_{RMS}}{P(CH1)_{RMS}}\right) \\ \text{AND} \\ \dfrac{\max(CH_3[\text{Seg Start}:\text{Seg End}]) - CH_3[\text{Seg Start}]}{\max(CH_1[\text{Seg Start}:\text{Seg End}]) - CH_1[\text{Seg Start}]} < \left(250\% \times \dfrac{P(CH3)_{RMS}}{P(CH1)_{RMS}}\right) \end{cases}$$

Then the results are combined:

$$\text{condition\_rise} = \begin{cases} \text{condition\_ch2\_rise} \\ \text{AND/OR} \\ \text{condition\_ch3\_rise} \\ \text{AND/OR} \\ \text{condition\_ch}_n\text{\_rise} \end{cases}$$

Candidate breath segments can also be processed in the time domain using a comparison with updated candidate breath power thresholds (step 123 of FIG. 2). In particular this allows artifacts which have similar characteristics but lower average power—for example rubbing between clothes and sensor—to be discounted as candidate breaths. As signal conditions change over time (such as the subject falling asleep), a threshold, which discerns breath sounds from other breath-like noise, may not be a fixed value. For example, high threshold values may not work when the subject is sleeping and low threshold values may reduce the discriminating capability of the system at other times. Hence, the comparison should be done with dynamically adapted thresholds.

A possible, but not only way to determine and update the thresholds is to evaluate the power of the envelope signal for some previously successfully detected breath events (with or without the noise floor subtracted), which can for example be calculated as:

$$P_{N,mean}(j) = \dfrac{\sum_{n=\text{Candidate Breath}_j \text{ Start}}^{\text{Candidate Breath}_j \text{ End}} CH_N(n)}{\text{Candidate Breath}_j \text{ Length}} \quad (6)$$

Where N represents the channel for which the power is being evaluated. Then the average of the different powers can be calculated and updated by incorporating more recent events into the calculation. For example, the average can be approximated
by using an IIR Infinite Impulse Response moving-average filter which provides a smoothed recent average $P_{mean}$ value. For example, the following transfer function (7) calculates the average power for every 20 breath sounds, where k is the index of breath sound considered in the calculation of $A_N$.

$$A_N(k) = \left(1 - \dfrac{1}{20}\right) \cdot A_N(k-1) + \dfrac{1}{20} \cdot P_{N,mean}(j) \quad (7)$$

For a breath signal segment to be selected as an actual breath the calculated power in one or a plurality of channels needs to be higher than, for example, a percentage of the mean dynamic power threshold. This percentage can be the same or different for different channels. A possible value would be 10%.

Finally, in order to avoid the effect of strong interference skewing the filtered value (for example, speech may be detected as breath due to the airflow in trachea), $A_N(k)$ can also be limited as for example is shown in equation (8).

$$A_N(k) = \begin{cases} A_N(k) \Rightarrow [\text{Eq. 7}] & \text{if } \dfrac{P_{N,mean}(j) - A_N(k-1)}{A_N(k-1)} \leq 50\% \\ A_N(k-1) \times 1.5 & \text{if } \dfrac{P_{N,mean}(j)}{A_N(k-1)} > 1.5 \\ A_N(k-1) \times 0.5 & \text{if } \dfrac{P_{N,mean}(j)}{A_N(k-1)} < 0.5 \end{cases} \quad (8)$$

The dynamic threshold is then calculated based on a fraction of the present value of $A_N(k)$, for example:

$$\text{Mean Power Threshold} = \dfrac{A_N(k)}{10}$$

Hence, for example, for increased apnea sensitivity any signal with mean power below the threshold can be discounted as a breath.

As previously described, "candidate segments" can be considered "breath segments" based on meeting a variable number of the criteria described before which will depend on the application. Furthermore, in some applications there may be "candidate segments" that may not pass the subset of conditions required for that particular application, but could still be subjected to extra evaluation steps as described below. For the purpose of explaining these further features of the method, segments that pass all the criteria before the power threshold evaluation will be referred to as "first class" segments; whereas a segment will be considered to be "second class" if it passes all the criteria including the power threshold evaluation except one or a few of the conditions.

Hence, in some applications, "first" and "second" class segments can be either directly upgraded to breath segments or be subjected to further extra scrutiny before finally being considered as a "breath" segment or not.

For example, if a particular application does not require a high sensitivity in the detection of apnea a possible method to further scrutinize whether a "first" or a "second class" segment can be upgraded can be a time location evaluation. For "second class" segments to be upgraded a sequence of n number of them (for example 10) have to be spread over time in the same way as would be expected of "first class" segments corresponding to a fraction of n breath cycles (for example 5) under the condition of full detection occurring (i.e. all inspirations and expirations being detected). After an upgrade of this kind, further "second class" segments being detected just after can also be upgraded if they fit the timing conditions in groups of two according to breath cycles.

In a similar way as presented previously, further time conditions can be used to upgrade a "second class" segment to a "first class segment if the time occurrence of it is considered appropriate based on the time location of its previous segments. In other words, whenever a group of, say, ten segments of any kind (first or second class) are found to fit the expected time location of five breath cycles (or other, n/2), any "second class" segment in the group can be upgraded.

It will be seen, therefore, that once the breath signal event is identified (where all or subset of the conditions presented before can be used for identification, depending on amongst other the system design constraints and the application), an accurate identification of true breath events can be provided. As a result the system can monitor a patient's breathing and, if breathing is detected to have ceased, issue an alarm or take other appropriate steps with improved accuracy and certainty.

It will be appreciated that the various features can be implemented in hardware or software as appropriate, in discrete or continuous time, in analogue or digital, running online or off-line.

Figure 7:
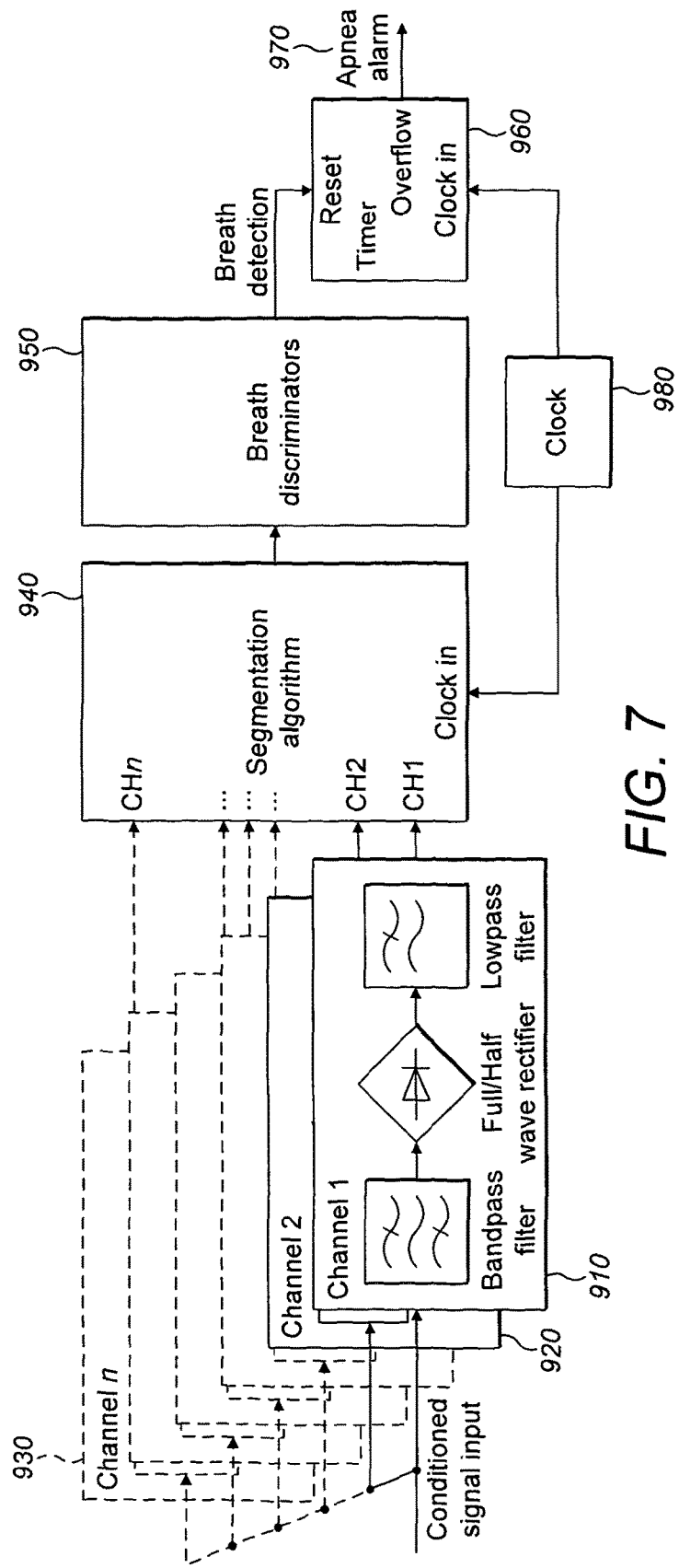
FIG. 7 shows an apnea detection system.

FIG. 7 shows a block diagram of the alarm systems according to one embodiment. At 910, 920, 930 the captured sound signal in respective bands is rectified and an envelope signal is produced. This is used by a segmentation and characterization module 940 to produce the 'candidate breaths'. A feature and similarity recognizer 950 analyses the channels and identifies actual breath inspiration or expiration events according to the techniques described herein.

Each time a breath inspiration or expiration event is detected, it triggers a timing event 960 using clock 980. It must be noted that system part 980 is not limited to one single embodiment and may generate more than one output such as one to control the timing for different processing steps of the method and another one for the apnea alarm counter. For example, to detect apnea, if no breath sound has been detected in a certain length of time, for example 25 seconds, the base station or the sensor system is enabled to produce an alarm signal 970. The system is also able to detect a gradual fall off in detected breath sounds, and again can be provided with a limit where the fall off becomes a danger to the patient. In the case where the alarm triggering block relies on the data being transmitted, a connection failure alarm can be raise if signal transmission is degraded. Similarly the same can be done for hardware and or software failures or for example if no meaningful data has been detected for a certain length of time. Any other appropriate steps, responses or analytical steps can be additionally or alternatively performed as can be understood from the discussion herein.

In addition to apnea detection, identified and characterized breath sounds together with the different evaluated parameters may be used for a variety of purposes, which are not limited to those described here. For example, the power of the signal within specific channels in either identified inspirations or expirations can be used to determine the subject's tidal volume. Furthermore the latter together with the timing characteristics of the signal can be used to determine respiratory flow (as this can be calculated from the derivative of the tidal volume). Also, candidate events for which there has been a decrease in power with respect to previously identified events can be used to identify hypopnoeas which are useful for diagnostic of a variety of conditions such as sleep apnea. Short identified apneas together with hypopnoeas can be used to identify mixed apneas which are again useful for sleep disorders diagnostics. Breathing rate can be calculated by counting candidate inspiration or expiration events. When looking to calculate respiratory rate (number of breath cycles per unit of time), each breath segment should be appropriately classified such that the correct grouping of segments into breath cycles can be done. This classification is important in order to count the number of respiratory cycles that have taken place in a given period of time, e.g. one minute (note each respiratory cycle consists of an inspiration and corresponding expiration, but in order to count the number of cycles only one of the two needs to be successfully identified). In order to do so information about the segments selected by the breathing detection method can be used.

One important piece of information is the minimum allowed segment duration for a segment. It is useful to know the minimum allowed duration of a segment so that when a section of time with no segments detection (i.e. a pause) is shorter than the minimum length threshold, then—with a high level of guarantee—that section of non-detection can be considered as one where no real breaths had occurred.

Regarding segment classification, a new technique can be used in order to recognize the breathing cycles where only one segment has been detected from those where both inspiration and expiration are detected. This can be done so that the appropriate number of respiratory cycles is calculated given that it is possible for either the inspiration or expiration of a breath cycle not to be detected. The approach is presented below in reference to FIG. 11 by means of different scenarios and where the word "segment" is used to refer to both first and second class segments. In FIG. 11 first class segments are depicted by a thick line on the upper section of the figure (examples labeled 'D'), second class segments are depicted by a thin line as well on the upper section of the figure (example labeled 'E') and second class segments that are upgraded to first class appear with both thick and thin lines such as the ones labeled 'F'.

Case 1: If a segment has a short time of non detections after it (i.e. a comparatively short pause until the next segment) and the previous segments are undefined with regards to the respiratory rate part of the algorithm, the segment under scrutiny can be classified as a first of a close group of segments and will be referred to as "initiator" (see label 'G' of FIG. 11).

The second segment in the group can be classified as "follower" (see label 'H' of FIG. 11). Here "short time" is defined by the time pause between the two segments being below a time threshold 'RRa', which is in the order of magnitude of a second. Initiators mostly correlate to inspirations because the pause between an expiration and the inspiration of the following breath cycle is mostly longer than threshold 'RRa' and also for an expiration to be considered "initiator" the previous segment should have been classified as either a follower or stand-alone (introduced later in case 3). Based on this it can be stated that the classification of an expiration as "initiator" is a more unlikely state of the algorithm than for inspirations. That said if a segment grouping shifted by one segment was to occur this would not greatly affect the performance.

Case 2: If a third detected segment is not close enough to the second and in turn has a fourth segment following closely, these third and fourth segments can be respectively classified as the "initiator" and "follower" of a new group of breaths as a breath cycle. Here "not close enough" and "following closely" are defined by being above a time threshold 'RRb' and below time threshold 'RRa' respectively. Hence, this sequence of segments would be, $1^{st}$ segment=initiator 1, $2^{nd}$ segment=follower1, $3^{rd}$ segment=initiator2, $4^{th}$ segment=follower2, where the numbers at the end of the words "initiator" and "follower" correspond to the breath cycle number in this example.

Case 3: Similarly if the third found segment is not close enough to the second (separated by more than time a threshold 'RRb', such as for example in label 'A' of FIG. 11 where a segment is not detected) and this time does not have a fourth segment following closely (longer than threshold 'RRa'), this third can be classified as a "stand alone" (see label 'I' of FIG. 11). Hence, this sequence of segments would be, $1^{st}$ segment=initiator 1, $2^{nd}$ segment=follower1, segment=stand-alone2, pause longer than threshold 'RRa'; where the numbers at the end of the words "initiator", "follower" and "stand-alone" correspond to the breath cycle number in this example.

Because of the selective criteria "stand alone" segments never have "followers". Because of this, the method will classify the next segment either as an "initiator" if it is followed closely (under threshold 'RRa') by another segment, or a "stand alone" again if the segment after it is separated to the next by a long enough time duration (above threshold 'RRa').

Case 4: As an exception, because a single breath signal can sometimes be split and be segmented into two parts (see labels 'B' and 'C' of FIG. 11), an exception exists for the case where an already existing group with a first (initiator) and second (follower), with these two segments particularly close together (below a time threshold 'RRc'), are closely followed (below time threshold 'RRb') by a third segment (see initiators labeled 'J' and 'L' in FIG. 11). In this case the third segment may be classified as an additional "follower" of that group provided the separations between all three of them fall within the given constraints (see labels 'K' and 'M' of FIG. 11). Here "particularly close together" are defined by the time separations between first and second being under time threshold 'RRc' and between second and third below time threshold 'RRb'. Hence, this sequence of segments would be, $1^{st}$ segment=initiator 1, $2^{nd}$ segment=follower1, $3^{rd}$ segment=follower1; where the number at the end of the words "initiator" and "follower" correspond to the breath cycle number in this example.

In parallel, thresholds 'RRa', 'RRb' and 'RRc' can vary over time as a function of the incoming signals from the breath detection algorithm. Additionally, other parameters can be inspected in order to achieve better judgment in the classification of initiators, followers and stand alones. Such parameters can be a variant of the segment end time point calculation or certain properties of the channel envelopes leading to other time separation measures such as the apex to apex separation for example.

Finally, in order to calculate respiratory rate (measured for example as respiratory cycles per minute) the number of initiators and stand alones present in the chosen time window (i.e. 1 minute) are counted or alternatively they can also be counted in a fraction of that window and then normalized. For example, the number of initiators and stand alones could be counted in 30 s and then extrapolated to a minute such as by multiplying by 2.

In one implementation obstructive apnea can be differentiated from central apnea by evaluating changes in power between a few last candidate events before the apnea, as well as a few breath events after the apnea. Also, the number of conditions that can be applied at a time may vary dynamically. For example, several consecutive candidate events may have been identified as inspiration followed by expiration (this can for example be done by evaluating the difference in time between an inspiration and an expiration within the same event and two consecutive inspirations and evaluating if those times remain constant within certain ranges which can also be dynamically updated). If a subsequent candidate event meets some but not all the conditions but happens at the time it was expected, that condition may be relaxed and the event may be classified as a true event.

Depending on the application it will be necessary to have a different tradeoff sensitivity/specificity and this will directly affect the number of conditions that should be imposed on the signal to truly determine whether a segment corresponds to an inspiration of expiration event or not. For example, in order to prevent critical situations such as sudden death a high sensitivity to apnea is necessary, which requires evaluation of all the conditions, and the average power can be a very important one. However, for breathing rate, considering candidate events that do not pass the average power conditions may result in a more precise calculation.

It will be noted that the appropriate described method can be adopted in any appropriate implementation, for example stress or concentration monitoring in the workplace or other areas such as military situations, and for humans or any other living creature.

Additionally it will be recognized that the system can store a unique subject specific code allowing immediate identification of the patient or individual being monitored. Hence the data can be immediately associated. Furthermore the data can be maintained secure by encryption for example by hashing with the user specific code. This code can also be the result of several inputs such as the date of the recording and additional identification parameters such as data of birth, motivation for recording, or else.

The breath detector or sensor system is preferably coated or encased in a structure composed of an appropriate material to achieve at least one of preventing water ingress, dust ingress, other foreign body ingress, isolating from electrical discharges, shielding from at least one type of ionizing or non-ionizing radiation, isolating from vibration or acoustic interference or temperature variations.

The particular components, circuitry and software/hardware adapted can vary as appropriate. For example any suitable signal detector can be used such as a sound or vibration transducer or accelerometer.

The invention claimed is:

1. A method of monitoring respiratory activity comprising:
   sensing a sound signal generated by a living human or animal body using a detector;
   separating the sound signal into more than two frequency bands using a processing apparatus;
   identifying a start point or an end point of an inspiration or expiration breath candidate by detecting as a feature of the sound signal a minimum or turning point, or based on a previous end point or start point using the processing apparatus;
   identifying a segment of the sound signal as a breath candidate based on the identified start point or end point using the processing apparatus;
   analyzing the segment of the sound signal identified as a breath candidate to detect an actual breath inspiration or expiration event using the processing apparatus; and
   taking one or more of the following actions:
       triggering an alarm or warning based on a timing of the actual breath inspiration or expiration event; or
       presenting a classification of the actual breath inspiration or expiration event in a visual, numeric, or auditory display.

2. The method of claim 1, further comprising applying a signal processing step to each separated band of the more than two frequency bands using the processing apparatus, and optionally wherein the signal processing step comprises at least one of subtracting an interference signal, scaling harmonics, delaying harmonics, filtering a DC signal, rectifying the sound signal, removing artifacts, smoothing the sound signal or filtering components above or below a frequency threshold.

3. The method of claim 1, further comprising comparing frequency band values to identify the breath candidate using the processing apparatus.

4. The method of claim 1, further comprising identifying, using the processing apparatus, a time at which the sound signal in at least one of the separated bands of the more than two frequency bands has risen a predetermined proportion from a predetermined threshold, and optionally wherein the predetermined threshold is at least one of:
dependent on at least a parameter of another separated band of the more than two frequency bands or on a previously used threshold; and
a function of a minimum or turning point.

5. The method of claim 4, further comprising measuring, using the processing apparatus, the signal-to-noise ratio for at least one separated band of the more than two frequency bands, and optionally further comprising identifying an end point within the fraction of a segment for which the signal-to-noise ratio is above or below a certain threshold.

6. The method of claim 1, further comprising identifying, using the processing apparatus, a signal noise floor, and optionally comprising identifying a respiratory pause and setting, as the signal noise floor, the minimum of a value of the sound signal during the respiratory pause, for at least one separated band of the more than two frequency bands, or setting, as the signal noise floor, the RMS value of the power of the signal integrated over a time within the respiratory pause, and further optionally comprising identifying a respiratory pause in each of a plurality of bands of the more than two frequency bands and setting a second noise floor as a function of the signal noise floor of said plurality of bands of the more than two frequency bands and/or further optionally comprising establishing as a third noise floor a function of the signal noise floors estimated during several previously identified respiratory pauses, or dynamically updating the noise floor in one or several bands of the more than two frequency bands.

7. The method of claim 1, comprising finding, using the processing apparatus, said feature of the sound signal based on a maximum value of the sound signal in at least one separated band of the more than two frequency bands after the candidate start point of a possible inspiration or expiration has been found, and optionally comprising identifying said feature of the sound signal when the sound signal in at least one separated band of the more than two frequency bands has fallen a certain proportion from its respective maximum or identified, as said feature of the sound signal, the slope at that point, and/or further optionally wherein the maximum is an absolute maximum in a candidate breath, or the slope value is the absolute slope, or comprising identifying said feature of the sound signal as a second minimum, or further comprising identifying the time value of occurrence of a second feature of the sound signal, or further comprising identifying for at least one separated band of the more than two frequency bands the duration of a possible expiratory or inspiratory phases from a measure of the difference between the time value of the first minimum and the time value when the sound signal has fallen a certain proportion from the respective maximum, and/or optionally further comprising identifying the duration of a possible expiratory or inspiratory phase from a fraction of the absolute difference between a function of the time of the second minimum or a turning point and the time at which the sound signal has risen a certain proportion from a function of the first minimum or a turning point from at least one separated band of the more than two frequency bands, or comprising identifying as a candidate inspiration or expiration event the fraction of the sound signal between the function of said two minimums or turning points.

8. The method of claim 1, further comprising analyzing, using the processing apparatus, envelope characteristics of separated bands of the more than two frequency bands to identify the breath candidate, or comparing the values between identified minimum and said proportion of a maximum or proportional rise from a minimum, and optionally comprising identifying a degree of mathematic monotonicity of at least one separated band of the more than two frequency bands within a predetermined time and/or optionally comprising identifying the breath candidate if a sound signal has a comparable envelope shape in two or more frequency bands of the more than two frequency bands, and/or optionally further comprising using the monotonicity information to identify the intervals of time during which a search of minimums or maximums should take place.

9. The method of claim 1, further comprising obtaining at least one functional relationship between equivalent parameters within separated bands of the more than two frequency bands, and optionally wherein the functional relationship is between values of a parameter of the processed sound signals which is correlated to power of the sound signal.

10. The method of claim 1, further comprising identifying, using the processing apparatus, the starting time of the breath candidate using information about monotonicity of one band of the more than two frequency bands, or a combined monotonicity of several bands of the more than two frequency bands and the minimum values of the processed sound signals in one or several bands of the more than two frequency bands, and optionally comprising comparing values of one or more relationships between parameters in the more than two frequency bands with a predetermined functional value, and identifying an event as a non-inspiration or non-expiration breath event if the comparison falls outside the predetermined value, and/or optionally further comprising identifying, as the breath candidate, a second sound signal having a parameter value greater than a proportion of the average value of preceding breath segments.

11. The method of claim 1, further comprising determining, using the processing apparatus, a number of breath candidates in a predetermined interval or a number of breath candidates having parameter values within a predetermined range for determination of a breathing condition, and optionally comprising detecting apnea if the number of breath candidates identified within a predetermined interval is lower than a predetermined threshold.

12. The method of claim 1, in which one or a plurality of measured parameters of at least one separated band of the more than two frequency bands is used to identify lung volume or respiratory rate related parameters.

13. The method of claim 1, further comprising determining, using the processing apparatus, a number of respiratory cycles in a predetermined interval based on a time location or separation of breath candidates in said interval for determination of respiratory rate.

14. The method of claim 13, further comprising generating, using the processing apparatus, an alarm if a proportion of the breath candidate detected in a certain time interval has measured characteristics that fall within predetermined critical limits.

15. The method of claim 1, further comprising storing, using the processing apparatus, at least one of: dynamically updating signal data, reproducing signal data, signal processing data, signal analysis data, a unique person specific code, or reconstruction of signal data from a set of determined parameters.

16. The method of claim 1, further comprising confirming, using the processing apparatus, a sequence of breath candidates based on a comparison with an expected temporal distribution, and optionally comprising classifying an event as inspiration or expiration based on preceding inspirations or expiration patterns, or comprising identifying an event as a candidate event if it deviates from previous candidate events patterns only within predetermined limits.

17. The method of claim 1 comprising outputting or storing data regarding the detected actual breath inspiration or expiration event.

18. The method of claim 1 comprising electronically transmitting information to a doctor or carer.

19. The method of claim 1 comprising making a diagnostic decision.

20. The method of claim 1 comprising making a management decision.

21. The method of claim 1 comprising making a treatment decision.

22. The method of claim 1, further comprising:
analyzing the separated sound signal within the different bands using a segmentation algorithm to define segments of the originally sensed signal as candidate breaths; and
evaluating the candidate segments within a certain time interval to identify a certain breath event.

23. The method of claim 1 wherein identifying a start point or an end point of an inspiration or expiration breath candidate comprises identifying a start point or an end point in each frequency band.

* * * * *